(12) United States Patent
Papp et al.

(10) Patent No.: US 7,097,440 B2
(45) Date of Patent: Aug. 29, 2006

(54) EMBOLIC PROTECTION SYSTEMS

(75) Inventors: John E. Papp, Temecula, CA (US);
Anuja Patel, San Jose, CA (US); Kent B. Stalker, San Marcos, CA (US);
Christopher Tarapata, North Andover, MA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 10/676,181

(22) Filed: Sep. 30, 2003

(65) Prior Publication Data

US 2004/0098032 A1    May 20, 2004

Related U.S. Application Data

(60) Division of application No. 09/896,142, filed on Jun. 29, 2001, now Pat. No. 6,656,202, which is a continuation-in-part of application No. 09/616,190, filed on Jul. 14, 2000, now Pat. No. 6,575,995.

(51) Int. Cl.
*B29C 33/76* (2006.01)
*A61M 29/00* (2006.01)

(52) U.S. Cl. .................. 425/112; 425/117; 425/393; 264/292; 606/200

(58) Field of Classification Search .............. 425/393, 425/112, 117; 606/200; 264/292
See application file for complete search history.

(56) References Cited

U.S. PATENT DOCUMENTS

| 4,171,943 A | * | 10/1979 | Tschanz et al. ............. 425/392 |
| 5,733,294 A | | 3/1998 | Forber et al. |
| 5,921,944 A | | 7/1999 | Borodulin et al. |
| 6,048,484 A | | 4/2000 | House et al. |
| 6,068,622 A | * | 5/2000 | Sater et al. ................ 604/524 |
| 6,325,815 B1 | * | 12/2001 | Kusleika et al. ............ 606/200 |
| 6,599,307 B1 | | 7/2003 | Huter et al. |
| 6,605,102 B1 | * | 8/2003 | Mazzocchi et al. ......... 606/200 |
| 6,656,202 B1 | | 12/2003 | Papp et al. |
| 2001/0000799 A1 | | 5/2001 | Wessman et al. |

FOREIGN PATENT DOCUMENTS

| WO | WO 96/01591 | 1/1996 |
| WO | WO 00/67670 | 11/2000 |
| WO | WO 01/10346 | 2/2001 |
| WO | WO 01/45592 | 6/2001 |
| WO | WO 01/49215 | 7/2001 |
| WO | WO 03/002028 A2 | 1/2003 |
| WO | WO 03/002028 A3 | 1/2003 |

* cited by examiner

*Primary Examiner*—Yogendra N. Gupta
*Assistant Examiner*—Thu Khanh T. Nguyen
(74) *Attorney, Agent, or Firm*—Fulwider Patton LLP

(57) ABSTRACT

A system for enabling the insertion and removal of an embolic protection device, for capturing and retaining embolic debris which may be created during the performance of a therapeutic interventional procedure in a stenosed or occluded region of a blood vessel. The system, in an embodiment thereof, enables the device to be snap-fitted so as to engage the distal end of a guide wire, to be pre-formed for expansion thereof so as to seal off the inner surface of a blood vessel, to inhibit the forming of a gap therein, for inhibiting embolic material from passing therethrough, and to be foreshortened to enable insertion thereof through confined spaces. The system, in another embodiment thereof, enables expandable material to be formed into an expandable configuration of an embolic protection device for capturing embolic material, which is capable of sealing off the inner surface of the blood vessel.

12 Claims, 15 Drawing Sheets

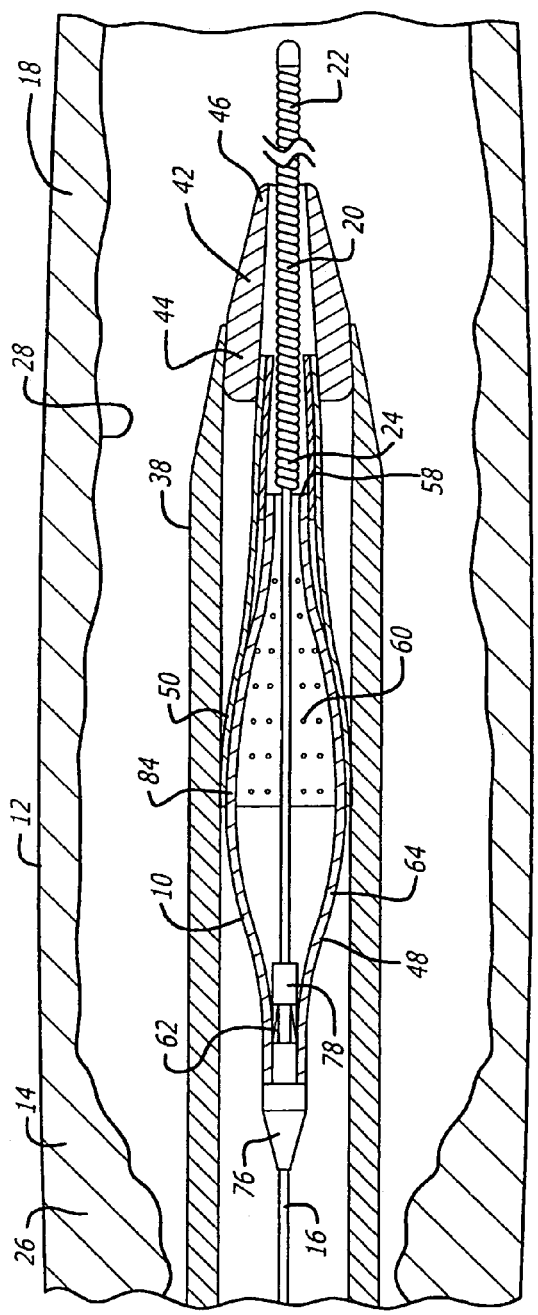
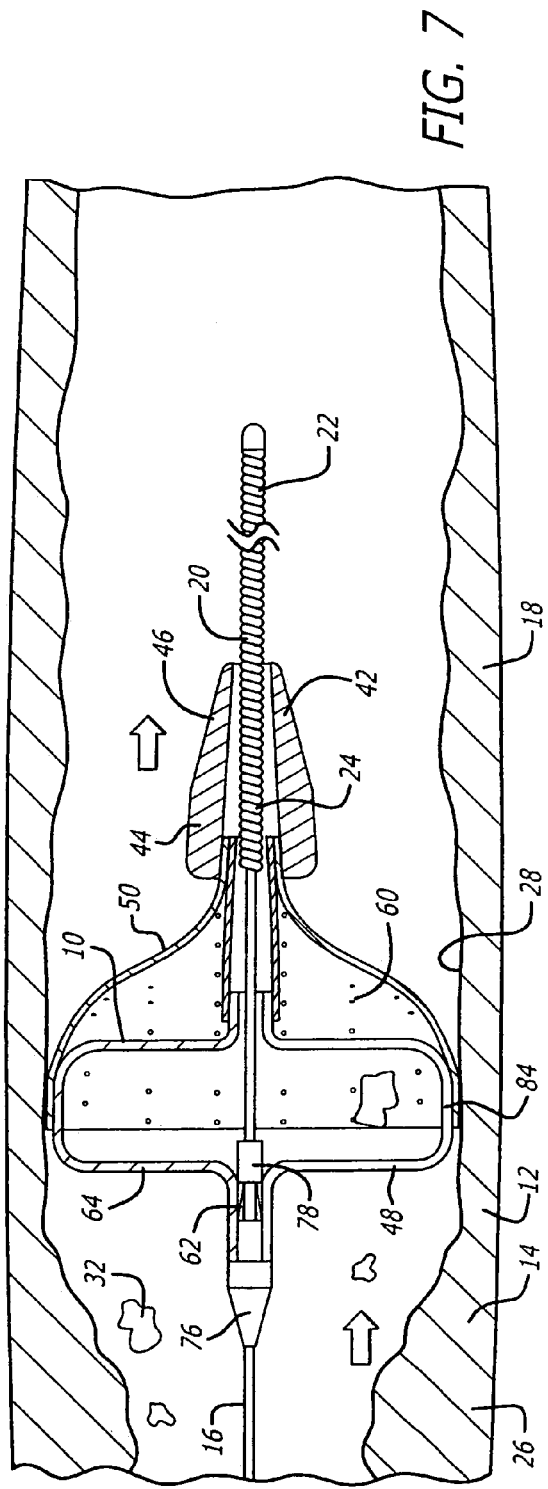

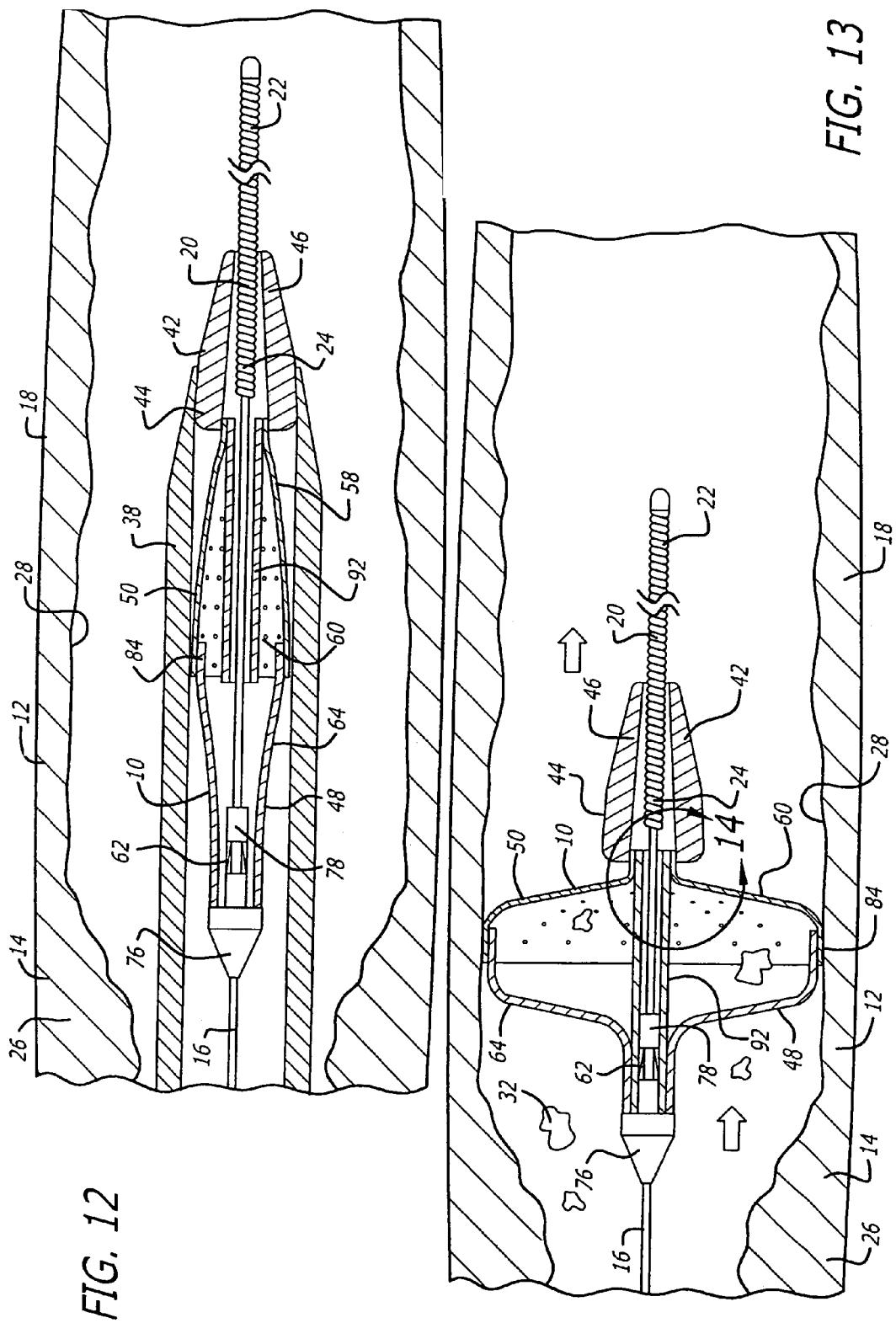

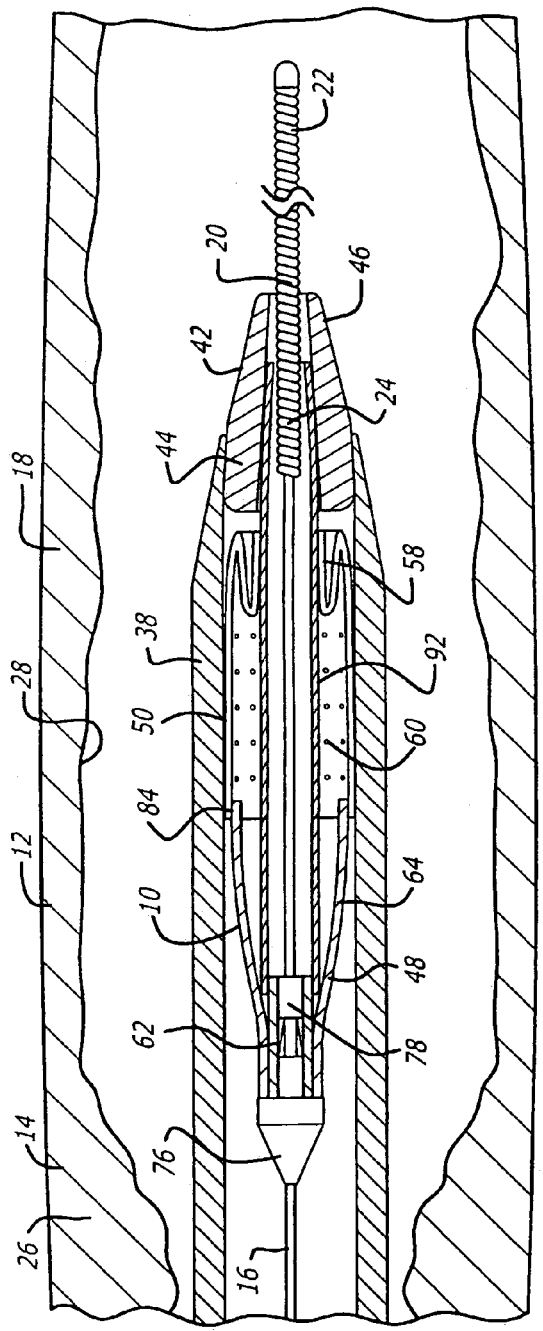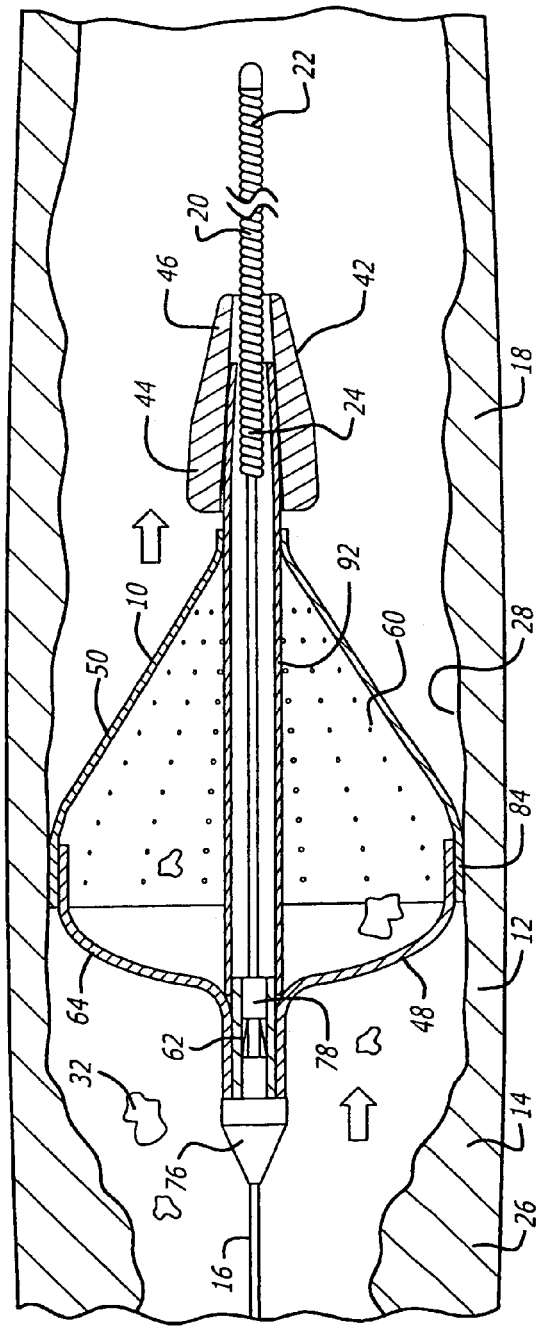

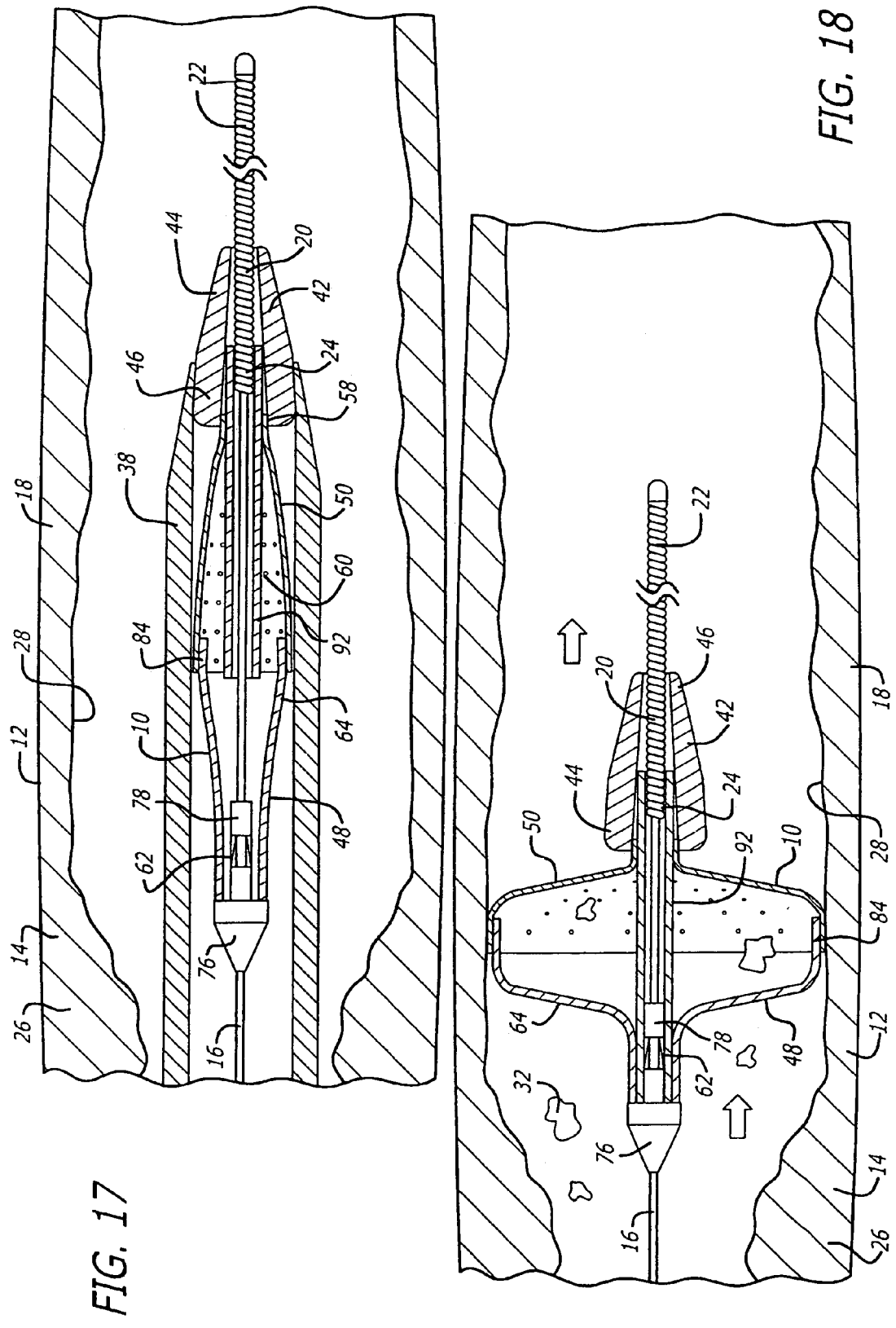

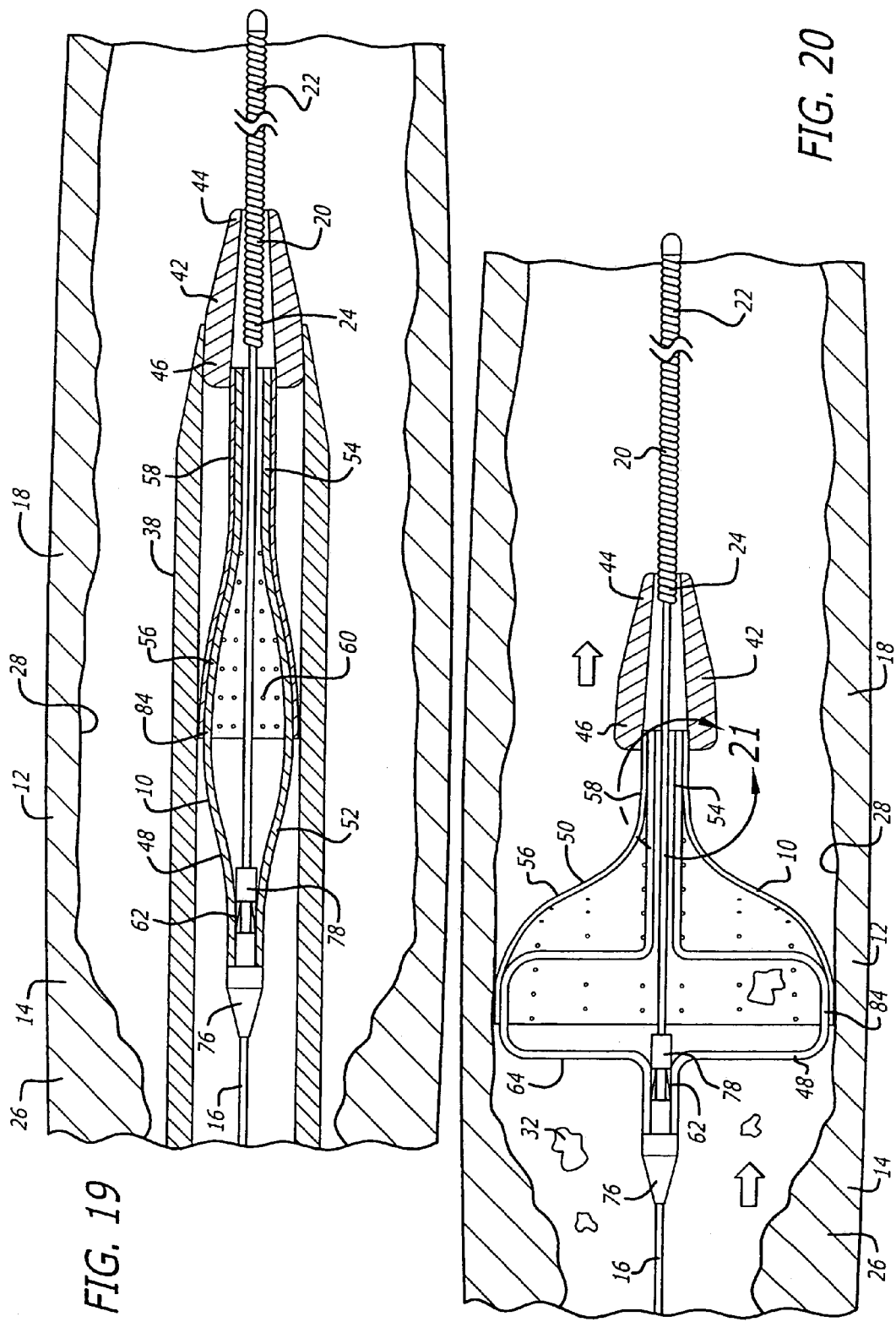

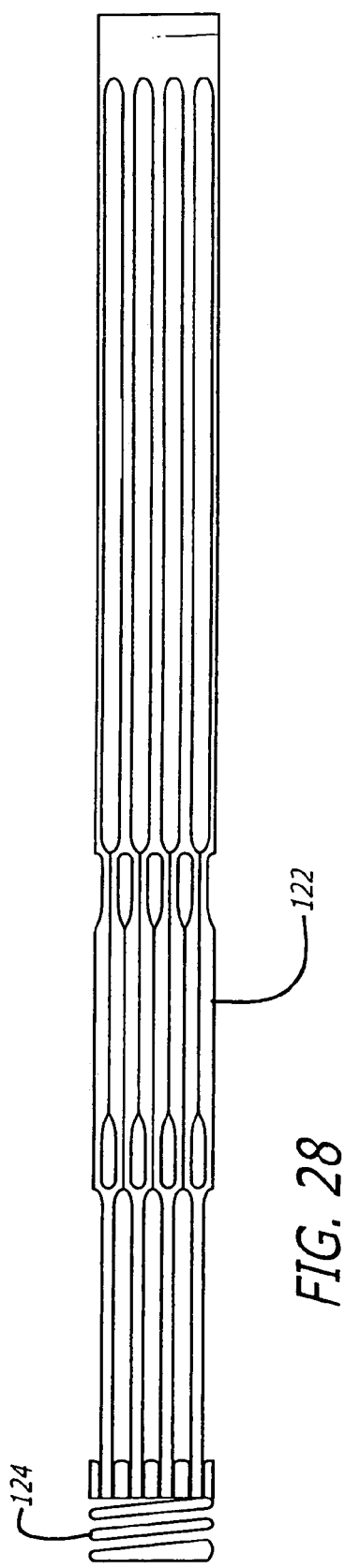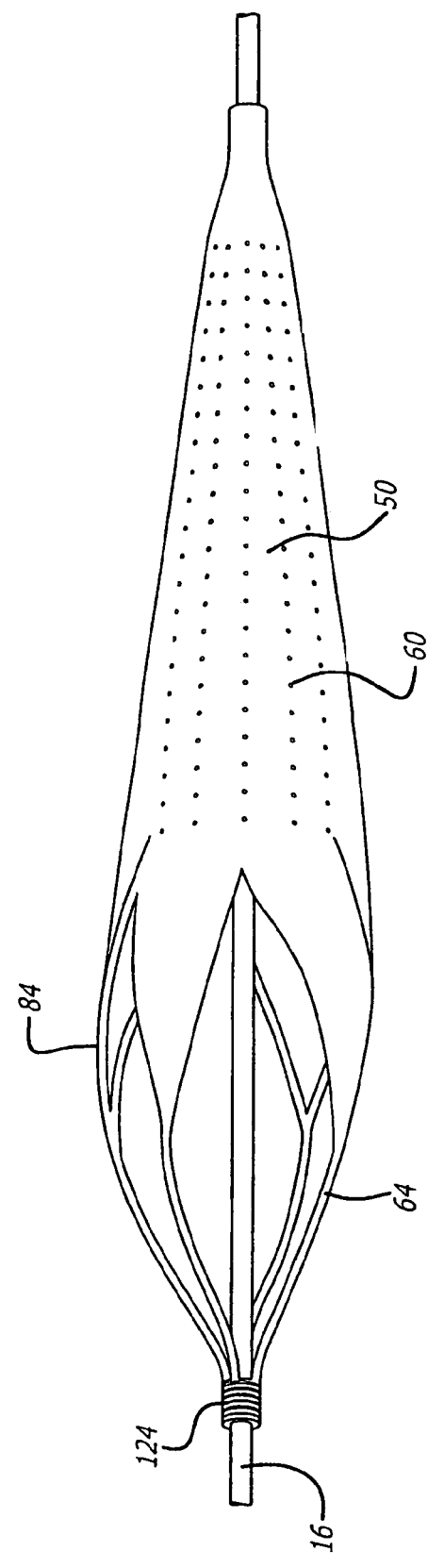

EMBOLIC PROTECTION SYSTEMS

RELATED APPLICATIONS

This is a divisional application of U.S. Ser. No. 09/896,142 filed on Jun. 29, 2001, now U.S. Pat. No. 6,656,202, which is a continuation-in-part of application Ser. No. 09/616,190 filed on Jul. 14, 2000, now U.S. Pat. No. 6,575,995.

BACKGROUND OF THE INVENTION

The present invention relates generally to improvements in embolic protection systems and methods. In particular, it relates to an improved system and method for enabling an embolic protection device to be efficiently and conveniently engaged with the distal end of a guide wire. The system also enables the device to effectively expand against the inner surface of a blood vessel wall, and to seal off the inner surface thereof upon deployment thereof at a location distal to an interventional procedure site. Such deployment enables the efficient capture of embolic material, which may be created and released into the bloodstream during the performance of the interventional procedure in a stenosed or occluded region of a blood vessel, and prevents embolic material from bypassing the embolic protection device. The system further enables the embolic protection device to be inserted through a patient's vasculature and to effectively navigate confined spaces therein, for deployment thereof at the location distal to the interventional procedure site.

The present invention further particularly relates to an improved system and method for efficiently forming expandable material into an expandable configuration of an embolic protection device, for capturing embolic material and preventing bypassing thereof. The expandable configuration of the device formed thereby provides a substantially uniform maximum outer diameter portion upon expansion thereof, to maintain vessel wall opposition upon deployment thereof, for preventing embolic material from bypassing the embolic protection device.

The systems and methods of the present invention are particularly useful when performing balloon angioplasty, stenting procedures, laser angioplasty or atherectomy in critical vessels, such as the carotid, renal, and saphenous vein graft arteries, where the release of embolic debris into the bloodstream could possibly occlude the flow of oxygenated blood to the brain or other vital organs which can cause devastating consequences to the patient.

A variety of non-surgical interventional procedures have been developed over the years for opening stenosed or occluded blood vessels in a patient caused by the build up of plaque or other substances on the walls of the blood vessel. Such procedures usually involve the percutaneous introduction of the interventional device into the lumen of the artery, usually through a catheter. One widely known and medically accepted procedure is balloon angioplasty in which an inflatable balloon is introduced within the stenosed region of the blood vessel to dilate the occluded vessel. The balloon catheter is initially inserted into the patient's arterial system and is advanced and manipulated into the area of stenosis in the artery. The balloon is inflated to compress the plaque and press the vessel wall radially outward to increase the diameter of the blood vessel.

Another procedure is laser angioplasty which utilizes a laser to ablate the stenosis by super heating and vaporizing the deposited plaque. Atherectomy is yet another method of treating a stenosed blood vessel in which a cutting blade is rotated to shave the deposited plaque from the arterial wall. A vacuum catheter may be used to capture the shaved plaque or thrombus from the blood stream during this procedure.

In another widely practiced procedure, the stenosis can be treated by placing a device known as a stent into the stenosed region to hold open and sometimes expand the segment of the blood vessel or other arterial lumen. Stents are particularly useful in the treatment or repair of blood vessels after a stenosis has been compressed by percutaneous transluminal coronary angioplasty (PTCA), percutaneous transluminal angioplasty (PTA) or removal by atherectomy or other means. Stents are usually delivered in a compressed condition to the target site, and then are deployed at the target location into an expanded condition to support the vessel and help maintain it in an open position.

In the past, stents typically have fallen into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self-expanding stent formed from, for example, shape memory metals or super-elastic nickel-titanum (NiTi) alloys, which will automatically expand from a compressed state when the stent is advanced out of the distal end of the delivery catheter into the body lumen. Such stents manufactured from self-expandable materials allow for phase transformations of the material to occur, contributing to the expansion and contraction of the stent.

The above non-surgical interventional procedures, when successful, avoid the necessity of major surgical operations. However, there is one common problem associated with all of these non-surgical procedures, namely, the potential release of embolic debris into the bloodstream which can occlude distal vasculature and cause significant health problems to the patient. For example, during deployment of a stent, it is possible that the metal struts of the stent can cut into the stenosis and shear off pieces of plaque which become embolic debris that can travel downstream and lodge somewhere in the patient's vascular system. Pieces of plaque material can sometimes dislodge from the stenosis during a balloon angioplasty procedure and become released into the bloodstream. Additionally, while complete vaporization of plaque is the intended goal during a laser angioplasty procedure, particles are not always fully vaporized and may enter the bloodstream.

When any of the above-described procedures are performed for example in the carotid arteries, the release of emboli into the circulatory system can be extremely dangerous to the patient. Debris that is carried by the bloodstream to distal vessels of the brain may cause these cerebral vessels to occlude, resulting in a stroke, and in some cases, death. Therefore, although carotid percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments enter the circulatory system following treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such procedures in the carotid arteries a high-risk proposition.

Other techniques which have been developed to address the problem of removing embolic debris include the use of catheters with a vacuum source which provides temporary suction to remove embolic debris from the bloodstream. However, as mentioned above, there have been complications with such systems since the vacuum catheter may not always remove all of the embolic material from the bloodstream, and a powerful suction could cause problems to the patient's vasculature.

Further techniques which have had some limited success include the placement of an embolic protection device such as a filter or trap downstream from the treatment site to capture embolic debris before it reaches the smaller blood vessels downstream. Such embolic protection devices enable the filtering of embolic debris which may be released into the bloodstream during the treatment to the vessel, and yet allow a sufficient amount of oxygenated blood to flow past the device to supply vital organs downstream from the treatment site.

However, there have been problems associated with embolic protection devices, particularly during the assembly, insertion, and deployment thereof. The device may be mounted on the guide wire in an inconvenient manner so as to be fixedly secured thereto. Also, the mounting of the device on the guide wire, such that the device is affixed to and rotatable with the guide wire, may result in the entangling of the device in a delivery sheath, upon the device being directed in the delivery sheath through the patient's anatomy to the position distal to the interventional procedure site. Further, the expansion and deployment of the embolic protection device may not result in full and complete expansion thereof, and consequently may not seal off the inner wall of the blood vessel about the entire circumference thereof, which can result in embolic material bypassing the device. The formation of the embolic protection device also may not be such as to enable the device to maintain vessel wall opposition upon expansion thereof, which can also result in the bypassing thereof by embolic material. The length of the device may further result in difficulty in navigating tortuous vasculature.

Therefore, the present invention provides improved systems and methods for treating stenosis in blood vessels which enable an embolic protection device to be efficiently assembled and to effectively navigate through a patient's vasculature for deployment at a location distal to an interventional procedure site. It also enables the device to expand so as to effectively seal off the inner surface of the blood vessel wall, to capture embolic material, and to prevent embolic material from bypassing the embolic protection device. The improved systems and methods of the present invention further enable the efficient formation of expandable material into an embolic protection device having a substantially uniform maximum outer diameter upon expansion thereof, to enable the effective capture of embolic material and prevent the bypassing thereof. Moreover, the systems and methods are relatively easy for a physician to use, while enabling the effective delivery and recovery of a filtering system capable of removing embolic debris released into the bloodstream. The inventions disclosed herein satisfy these and other needs.

SUMMARY OF THE INVENTION

The present invention, in general, provides a system and method for enabling the insertion and removal of a filtering system for capturing and retaining embolic debris from a blood vessel. The embolic debris may be created during the performance of a therapeutic interventional procedure, such as a balloon angioplasty or stenting procedure. The filtering system prevents the embolic debris from lodging and blocking blood vessels downstream from the interventional site. The present invention is particularly useful for enabling an interventional procedure to be performed in vital arteries, such as the carotid arteries, in which critical downstream blood vessels can become blocked with embolic debris, including the main blood vessels leading to the brain or other vital organs. As a result, the present invention provides the physician with a higher degree of confidence in the efficient operation of a filtering system for the collection and removal of embolic debris from the blood vessel when performing high-risk interventional procedures.

The present invention enables a filtering system to be deployed in the blood vessel at a location distal to the area of treatment in the interventional procedure site. It also enables the blood to pass therethrough to enable blood to flow past the filter. It further enables the blood to be filtered to capture and retain any embolic debris which may be created during the interventional procedure.

More particularly, for example, in an embodiment of the present invention, a system is provided for enabling the effective assembly thereof for engagement with a guide wire. The present invention also enables the system to expand against the inner surface of a wall of a blood vessel so as to efficiently seal off the inner surface thereof, for enabling the capture of embolic material which may be released into the blood vessel during the therapeutic interventional procedure. Further, the system enables navigation thereof through a patient's blood vessel, including tortuous vasculature, to a position distal to an interventional procedure site, for deployment of the embolic protection device.

The system includes a guide wire, including a distal end, which is positionable within the blood vessel so as to extend to a position distal to an interventional procedure site. The system also includes a filter device, which is snap-fittable so as to engage the distal end of the guide wire, for effective and convenient engagement therewith. The filter device is deployed at the location in the patient's vasculature distal to the interventional procedure site, so as to capture embolic material which may be released into the blood in the blood vessel during the interventional procedure. The filter device includes a pre-formed expandable shape thereof, including a pre-formed expandable maximum outer diameter portion thereof. The pre-formed expandable maximum outer diameter portion enables the filter device to effectively expand against the inner surface of the wall of the blood vessel, and to extend along and seal off the inner surface of a wall of the blood vessel, upon expansion of the filter device for deployment thereof. Such expansion of the maximum outer diameter portion of the filter device inhibits the formation of a gap between the filter device and the blood vessel wall, through which embolic material may otherwise flow. The filter device is foreshortened, such that the length thereof is shortened to enable efficient insertion thereof through confined spaces in the patient's blood vessel.

In another embodiment of the present invention, for example, a system is provided which enables expandable material to be effectively formed into an expandable configuration of a cage for a filter device, for pre-forming the cage so as to enable the filter device to capture embolic material which may be released into a blood vessel during a therapeutic interventional procedure upon expansion thereof. The expandable configuration of the cage to be pre-formed by the system provides a substantially uniform pre-formed expandable maximum outer diameter thereof, for maintaining vessel wall opposition in a patient's vasculature upon deployment of the basket at a location distal to an interventional procedure site.

The system includes a male mandrel element, which enables the expandable material to be extended thereover. The male mandrel element includes a main section, which includes a maximum outer diameter extending along the length thereof which is substantially uniform, and is substantially equal to the maximum inner diameter of the expanded configuration of the cage to be formed thereby. The system further includes a female die element, which enables the expandable material to be formed therein. The female die element includes a main section, which extends over the main section of the male mandrel member and the expandable material. The female die element also has a cavity therein, the length of which extends for at least a portion of the length of the main section of the male mandrel member. The maximum diameter of the cavity in the female die element is substantially uniform, and is substantially equal to the maximum outer diameter of the expanded configuration of the cage to be formed thereby.

The above objects and advantages of the present invention, as well as others, are described in greater detail in the following description, when taken in conjunction with the accompanying drawings of illustrative embodiments.

BRIEF DESCRIPTION OF THE DRAWINGS

FIG. 6 is an elevational fragmentary partly-sectional view of a second version of the first embodiment of the present invention, disposed within the internal carotid artery of a patient, including a delivery sheath and an unexpanded filter device.

FIG. 7 is a similar view of the second version of the first embodiment shown in FIG. 6, wherein the delivery sheath has been removed and the filter device has expanded.

FIG. 12 is a similar view as in FIG. 10, depicting another form of a filter device in the third version of the first embodiment of the invention, within a delivery sheath.

FIG. 13 is a similar view of the other form of the third version of the first embodiment shown in FIG. 12, wherein the delivery sheath has been removed and the filter device has expanded.

FIG. 15 is an elevational fragmentary partly-sectional view of a form of a fourth version of the first embodiment of the present invention, disposed within the internal carotid artery of a patient, including a delivery sheath and an unexpanded filter device.

FIG. 16 is a similar view of the fourth version of the form of the first embodiment shown in FIG. 15, wherein the delivery sheath has been removed and the filter device has expanded.

FIG. 17 is a similar view as in FIG. 15, depicting another form of a filter device in the fourth version of the first embodiment of the invention, within a delivery sheath.

FIG. 18 is a similar view of the other form of the fourth version of the first embodiment shown in FIG. 17, wherein the delivery sheath has been removed and the filter device has expanded.

FIG. 19 is an elevational fragmentary partly-sectional view of a fifth version of a first embodiment of the present invention disposed within the internal carotid artery of a patient, including a delivery sheath and an unexpanded filter device.

FIG. 20 is a similar view of the fifth version of the first embodiment seen in FIG. 19, wherein the delivery sheath has been removed and the filter device has expanded.

FIG. 28 is a plan view of a flattened rolled out form of the tube in FIG. 27, in the second embodiment of the invention.

FIG. 29 is an elevational view of a filter device including a cage formed by the system of the second embodiment.

DETAILED DESCRIPTION OF THE PREFERRED EMBODIMENTS

Figure 1:
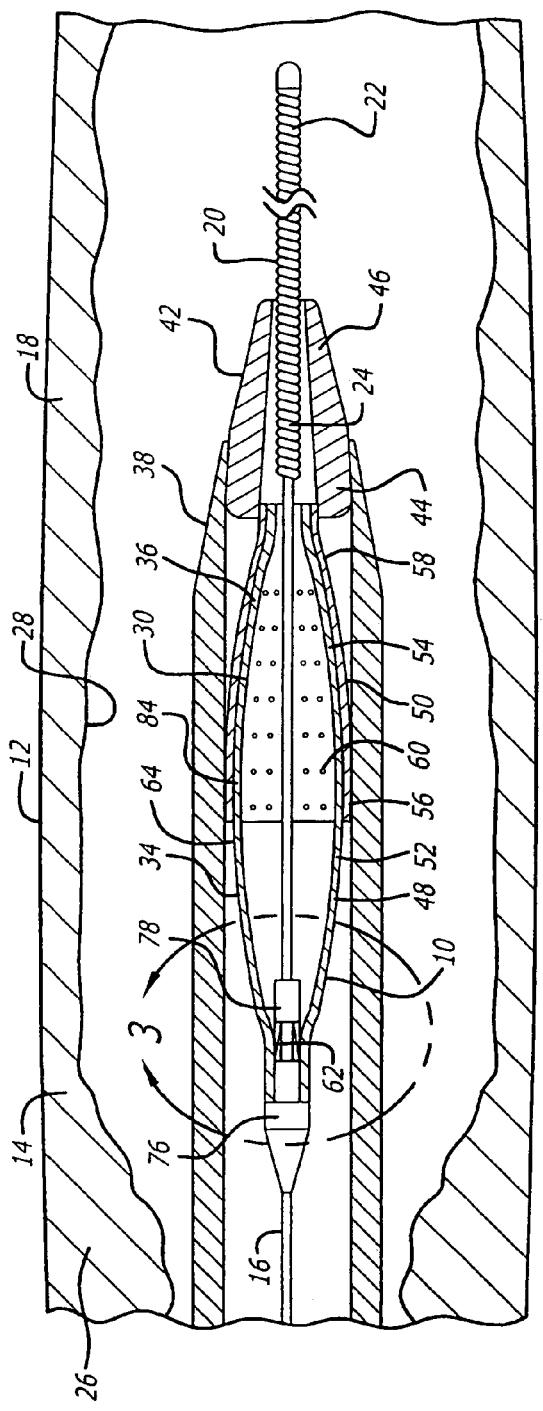
FIG. 1 is an elevational fragmentary partly-sectional view of a form of a first version of a first embodiment of the present invention, disposed within the internal carotid artery of a patient, including a delivery sheath and an unexpanded filter device.

The present invention is directed to an improved system and method for enabling the capture of embolic material which may be released into the blood vessel during the therapeutic interventional procedure, in an efficient and effective manner. The invention enables a filter device to be snap-fitted to a guide wire for effective and convenient engagement therewith. It is further directed to a filter device which provides a pre-formed expandable shape, for expanding against and sealing off the inner surface of the wall of a blood vessel, to inhibit the formation of a gap through which embolic material may otherwise flow. The present invention further enables rotational movement of the filter device independent of rotational movement of the guide wire, and inhibits translational movement of the filter device. The length of the filter device is also foreshortened, relative to the length of prior filter devices, so as to be less affected by confined spaces, including curves and sharp bends in the patient's anatomy.

The present invention is further directed to an improved system and method which enables expandable material to be formed into an expandable configuration of a basket, for forming a cage for a filter device for capturing embolic material which may be released into a blood vessel during a therapeutic interventional procedure. The expandable configuration of the cage to be formed by the system provides a substantially uniform maximum outer diameter thereof, for maintaining vessel wall opposition in the patient's vasculature upon deployment of the cage at a location distal to an interventional procedure site.

The embodiments of the improved system and method are illustrated and described herein by way of example only and not by way of limitation. While the present invention is described as applied to the carotid arteries of the patient, those skilled in the art will appreciate that it can also be used in other body lumens as well, such as the coronary arteries, renal arteries, saphenous veins and other peripheral arteries. Additionally, the present invention can be utilized when performing any one of a number of interventional procedures, such as stenting, balloon angioplasty, laser angioplasty or atherectomy.

In reference to the drawings, wherein like reference numerals denote like or corresponding parts throughout the drawing figures, and particularly to FIGS. 1–29, in the embodiments of a system and method in accordance with the invention, for example, a system 10 is provided for enabling an interventional procedure to be performed in a blood vessel 12 at an area of treatment 14. The system 10 is adapted to be atraumatic. It includes a guide wire 16 which enables the system 10 to be positioned distal to the area of treatment 14. The system 10 is placed within the carotid artery 18 or other blood vessel of the patient, and is guided into position by the guide wire 16. The guide wire 16 includes a tip coil 20 at a distal end 22 thereof. The tip coil includes a proximal end 24. The carotid artery 18 has the area of treatment 14 therein, which comprises the interventional procedure site, wherein atherosclerotic plaque 26 has built up against the inside wall 28, which decreases the diameter of the carotid artery 18. As a result, blood flow is diminished through this area.

The therapeutic interventional procedure comprises implanting an expandable interventional instrument at the interventional procedure site 14, to press the build-up of plaque 26 of the stenosis against the inside wall 28, to increase the diameter of the occluded area 14 of the artery 18, and to help restore sufficient flow of blood to the downstream vessels leading to the brain. The expandable interventional instrument not only helps increase the diameter of the occluded area, but helps prevent restenosis in the area of treatment 14. The interventional instrument is expandable upon deployment thereof at the interventional procedure site 14.

The system 10 of the present invention enables the delivery of a filter device 30 to a location distal to the area of treatment 14, to enable deployment of the filter device 30 at the location distal to the area of treatment 14, and to enable the removal of the filter device 30 from the delivered and deployed position thereof. The filter device 30 filters the blood in the blood vessel 12, so as to pass blood therethrough and capture embolic material 32 which may be released in the blood vessel 12 during the interventional procedure. It engages the distal end 22 of the guide wire 16, so as to enable the filter device 30 to be placed within the carotid artery 18 or other blood vessel of the patient and guided into position distal to the area of treatment 14. The filter device 30 includes a proximal portion 34 and a distal portion 36.

Referring to FIGS. 1–21, in a first embodiment of a system pursuant to the present invention, for example, the system 10 enables movement thereof through the patient's blood vessel 12 to a position distal to the area of treatment 14 for deployment of the filter device 30. The system 10 further enables expansion of the filter device 30 against the inside wall 28 of the blood vessel 12 and the sealing off of the inside wall 28, to enable the capture of embolic material 32 which may be released into the blood vessel 12 during the therapeutic interventional procedure.

The system 10 in accordance with the first embodiment of the invention includes the guide wire 16, positionable within the blood vessel 12, and extendable to a position distal to the interventional procedure site 14. The system 10 further includes the filter device 30, which is snap-fitted for engagement with the distal end 22 of the guide wire 16. The filter device 30 extends within a delivery sheath 38 for delivery to the interventional procedure site 14. The delivery sheath 38 includes a distal portion 40. The system 10 further includes an obturator 42, which includes a proximal end 44 and a distal end 46. The obturator 42 extends between the delivery sheath 38 and the tip coil 20; such that the distal end 46 of the obturator 42 extends along the proximal end 24 of the tip coil 20, and the proximal end 44 of the obturator 42 is substantially abutted by the distal portion 40 of the delivery sheath 38 when the delivery sheath 38 is extended over the filter device 30. The obturator 42 provides a smooth transition between the delivery sheath 38 and the tip coil 20, so as to slide smoothly around tortuous anatomy in the blood vessel 12, and to inhibit digging into the inside wall 28 of the blood vessel 12 thereby.

The filter device 30 is deployed at the location in the patient's blood vessel 12 distal to the area of treatment 14, upon withdrawal of the delivery sheath 38. It captures embolic material 32 which may be released into the blood in the blood vessel 12 during the interventional procedure. The length of the filter device 30 is foreshortened, to enable the filter device 30 to extend through confined spaces such as corners and sharp bends while retaining opposition to the vessel inside wall 28, and to inhibit collapsing thereof which otherwise may result in loss of opposition to the inside wall 28 of the blood vessel 12. Upon being snap-fitted onto the distal end 22 of the guide wire 16, the filter device 30 engages the guide wire 16, and enables rotation of the filter device 30 independent of rotation of the guide wire 16, while inhibiting translation thereof along the guide wire 16.

In the first embodiment in accordance with the invention, as illustrated in FIGS. 1–21, the length of the filter device 30 is foreshortened, to enable the filter device 30 to negotiate confined spaces in the patient's vasculature. The filter device 30 includes a cage 48, which is snap-fitted onto the distal end 22 of the guide wire 16 for engagement therewith, and filter material 50, for filtering embolic material 32, secured to the cage 48. The cage 48 includes a proximal portion 52 and a distal portion 54, and the filter material 50 includes a proximal end 52, a distal end 54, and a plurality of holes 60 therein for filtering embolic material 32.

Figure 3:
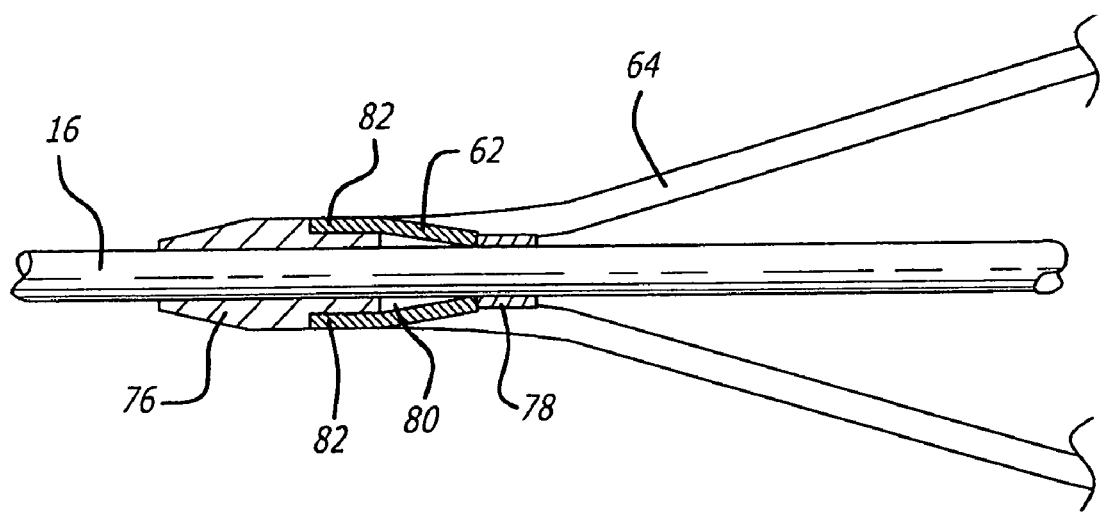
FIG. 3 is a partly cross-sectional view taken along the line 3—3 of FIG. 1.
Figure 5:
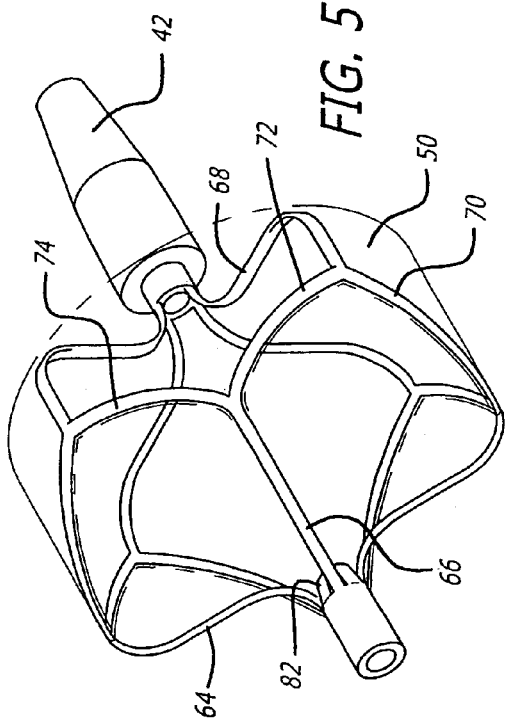
FIG. 5 is a perspective view of the expanded filter device shown in FIG. 4.
Figure 8:
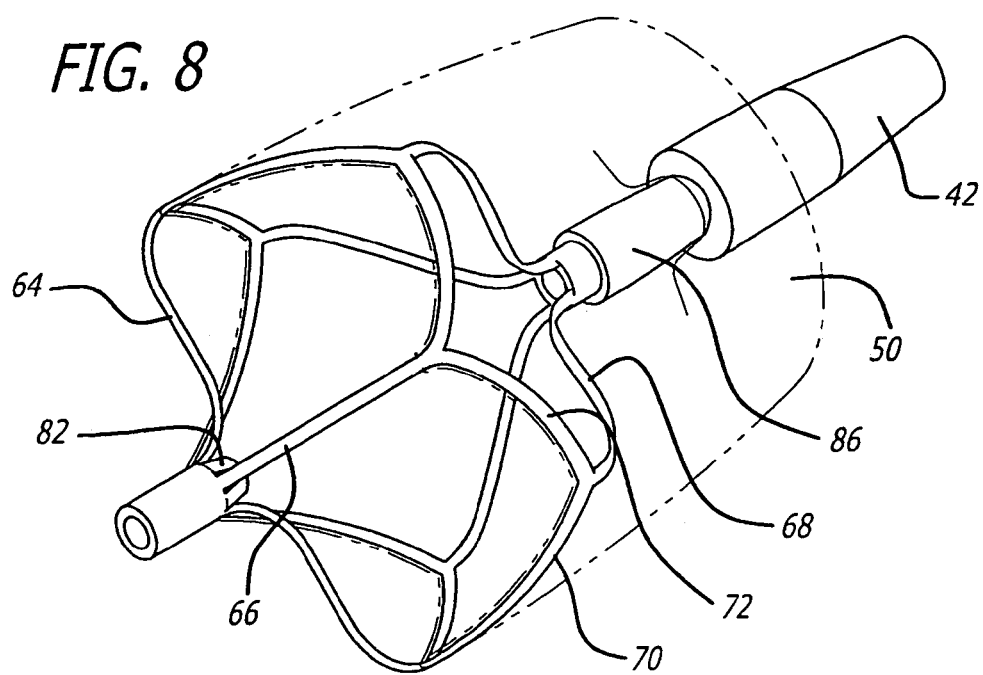
FIG. 8 is a perspective view of the expanded filter device shown in FIG. 7.
Figure 9:
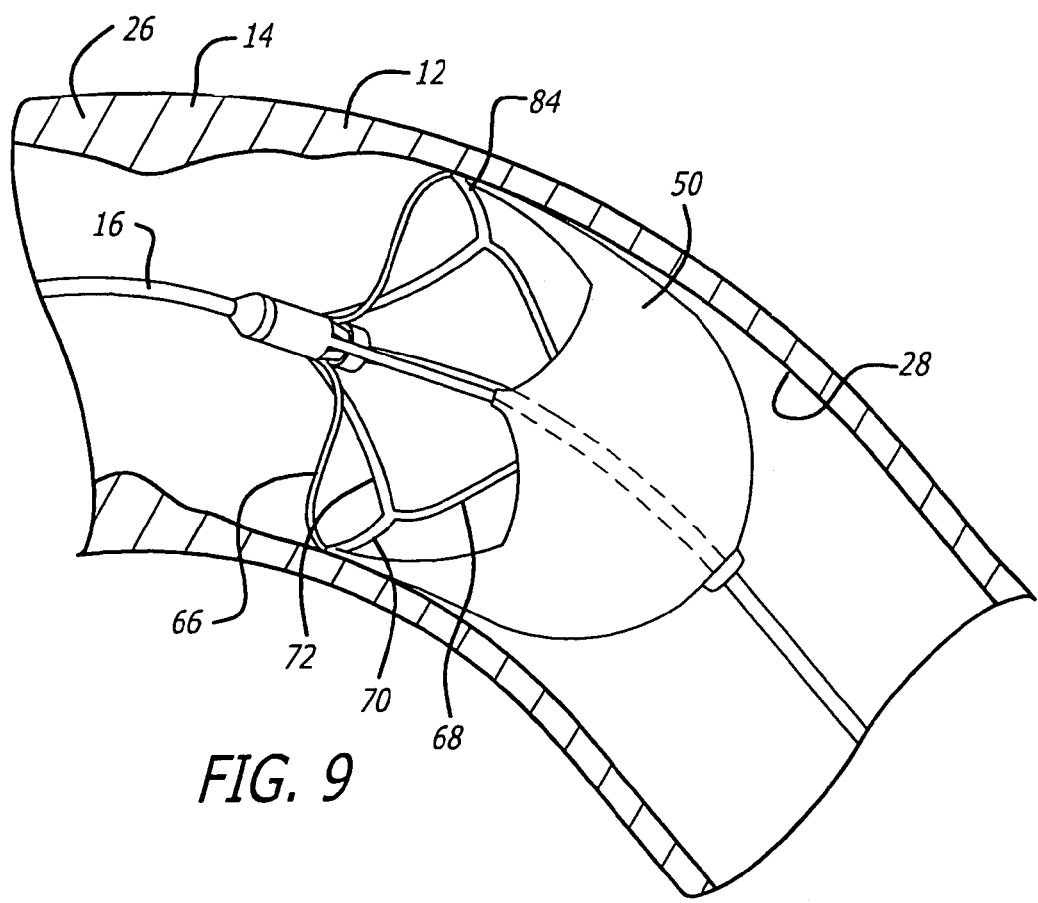
FIG. 9 is a similar view of the expanded filter device shown in FIG. 8, within the internal carotid artery of a patient.

The cage 48 further includes an engaging element 62, located at the proximal portion 52 thereof, as shown in enlarged view in FIG. 3, for enabling the cage 48 to snap-fit so as to engage the distal end 22 of the guide wire 16. The engaging element 62 is adapted to enable the cage 48 to be snap-fitted onto the distal end 22 of the guide wire 16. The cage 48, upon being snap-fitted onto the distal end 22 of the guide wire 16, is adapted to enable rotational movement of the cage 48 independent of rotational movement of the guide wire 16, and to inhibit translational movement of the cage 48 along the guide wire 16. The cage 48 further includes a plurality of struts 64. As depicted in FIG. 5, the plurality of struts 64 comprise a plurality of proximal ribs 66, a plurality of distal ribs 68; and a ring 70, which extends intermediate the plurality of proximal ribs 66 and the plurality of distal ribs 68. The ring 70, for example, includes a plurality of segments 72 and 74, and each adjacent pair of the plurality of segments 72 and 74 forms a generally v-shaped section of the ring 70.

The system 10 further includes a proximal stop 76 and a distal stop 78, adapted to be secured to the distal end 22 of the guide wire 16, and having a space 80 between the proximal stop 76 and the distal stop 78. The engaging element 62 of the cage 48 is adapted to be snap-fitted to the proximal stop 76 and the distal stop 78 in the space 80 therebetween. The engaging element 62 includes at least one tab 82, which is bent inwardly, for example, for engaging the proximal stop 76 and the distal stop 78 in the space 80 between the proximal stop 76 and the distal stop 78.

The cage 48 further includes a pre-formed expandable shape, which comprises a heat-treated shape, and which includes a pre-formed expandable maximum outer diameter portion 84, for expanding against the inside wall 26 of the blood vessel 12 upon expansion of the cage 48 for deployment thereof. Upon such expansion thereof, the maximum outer diameter portion 84 of the cage 48 also extends along and seals off the inside wall 28 of the blood vessel 12, to inhibit the formation of a gap between the cage 48 and the blood vessel inside wall 28 through which embolic material 32 may otherwise flow. The ring 70 forms the maximum outer diameter portion 84 of the cage 48. The proximal end 56 of the filter material 50 is secured to the maximum outer diameter portion 84 of the cage 48.

Figure 2:
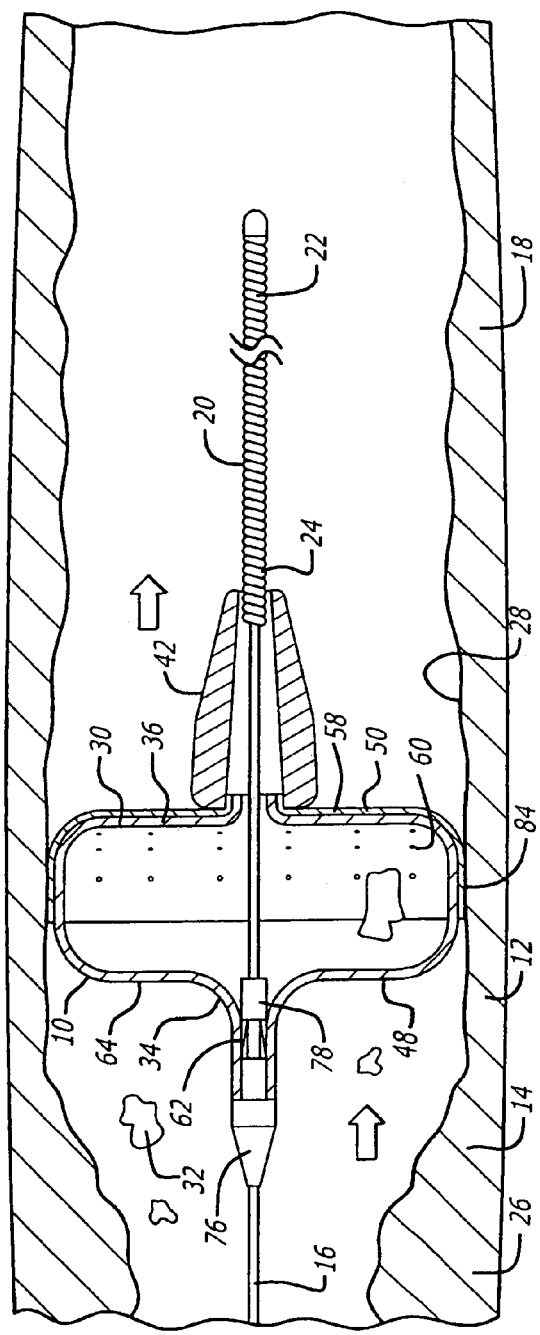
FIG. 2 is a similar view of the form of the first version of the first embodiment shown in FIG. 1, wherein the delivery sheath has been removed and the filter device has expanded.

In a first version of the first embodiment of a system pursuant to the present invention, as shown in FIGS. 1–5, the cage 48 is foreshortened, whereby the length thereof is between about 1 centimeter to 1.5 centimeters, as compared to a length of prior cages of about 2 centimeters. The heat-treated expanded shape of the cage 48, in the form thereof shown in FIG. 2, is generally rectangular or cylindrical. In the form of the cage 48 illustrated in FIG. 4, the plurality of proximal ribs 66 are generally s-shaped, which enables the plurality of struts 64 to absorb pulsations in the patient's vasculature. Alternatively or in addition thereto, the plurality of distal ribs 68 may be generally s-shaped for enabling such pulsation absorption.

As illustrated in FIGS. 6–9, in a second version of the first embodiment in accordance with the invention, the cage 48 is foreshortened. The filter material 50 expands out from the cage 48, without being confined to the shape of the cage 48, generating a larger volume of the filter material 50 for the collection of embolic material 32. The flow of blood generates the expansion of the filter device 30 into its deployed shape. The filter material 50 may be coated with a suitable coating or surface treatment to inhibit it from sticking to itself and not deploying. The substantial surface area of the filter material 50 may further have additional holes 60 therein to enable increased blood flow therethrough. A spacer 86 includes a proximal end 88, and a distal end 90. The proximal end 88 of the spacer 86 extends on top of the distal portion 54 of the cage 48, and the distal end 90 of the spacer 86 extends on top of the proximal end 24 of the tip coil 20. Alternatively, the spacer 86 may extend in the space between the distal portion 54 of the cage 48 and the proximal end 24 of the tip coil 20. The spacer 86 enhances the deployment of the filter material 50 and inhibits collapsing thereof.

Figure 10:
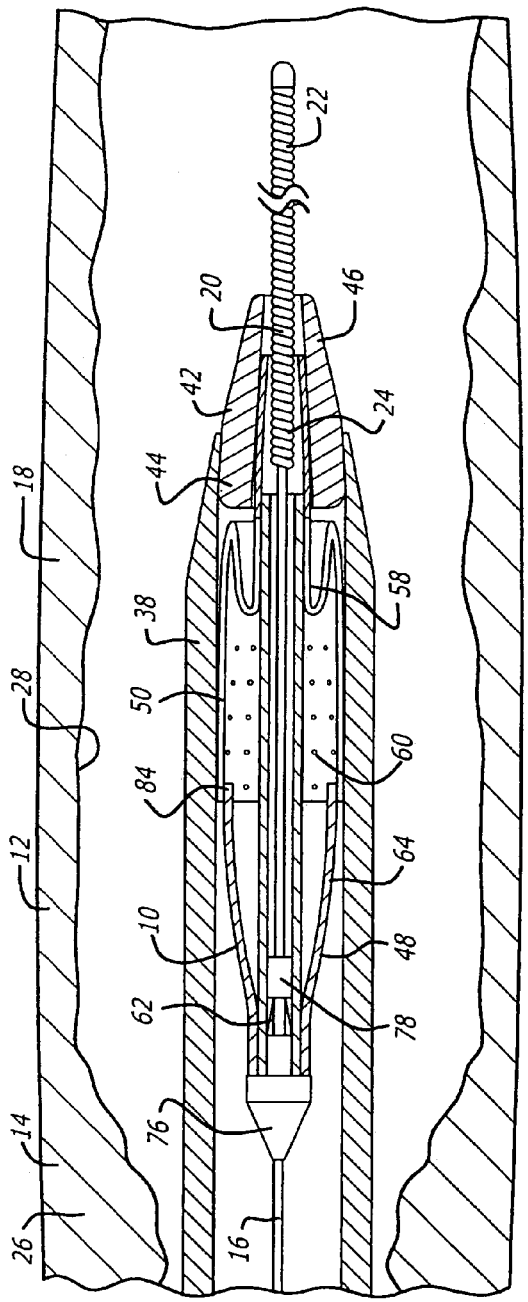
FIG. 10 is an elevational fragmentary partly-sectional view of a form of a third version of the first embodiment of the present invention, disposed within the internal carotid artery of a patient, including a delivery sheath and an unexpanded filter device.
Figure 11:
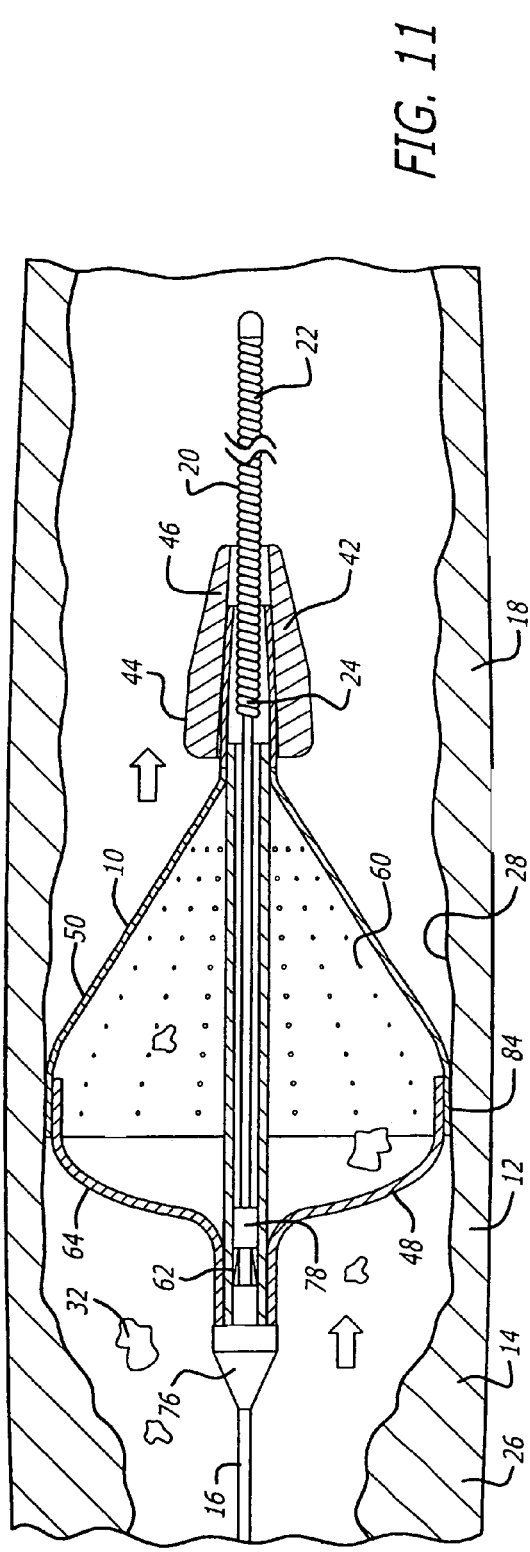
FIG. 11 is a similar view of the form of the third version of the first embodiment shown in FIG. 10, wherein the delivery sheath has been removed and the filter device has expanded.

The cage 48, in a third version of the first embodiment pursuant to the present invention, as seen in FIGS. 10–14, is foreshortened, and comprises the proximal portion 52 thereof which does not include a distal portion 54 thereof. In the form thereof shown in FIGS. 10–11, the distal end 58 of the filter material 50 is folded over, prior to expansion thereof, as seen in FIG. 10, and expands upon deployment thereof, as depicted in FIG. 11. The filter device 30 further includes a hypotube 92 extending therein, which includes a proximal portion 94 and a distal portion 96. In the form of FIGS. 10–11, the hypotube 92 extends substantially the length of the cage 48. In the form in FIGS. 12–13, the proximal portion 94 of the hypotube 92 is spaced from the proximal end 56 of the cage 48 prior to deployment, and moves into position abutting the proximal end 56 of the cage 48 upon deployment thereof. The distal portion 96 of the hypotube 92 is variably flexible, and includes slots 98 therein, as shown in an enlarged view in FIG. 14, to provide a substantially uniformly increasing flexibility profile towards the distal portion 96 thereof. An extended part of the proximal end 44 of the obturator 42 extends over an extended part of the distal end 58 of the filter material 50, such that the profile of the filter device 30 is narrowed towards the distal portion 36 thereof, to inhibit filter bulging upon recovery of the filter device 30 filled with embolic material 32.

Figure 14:
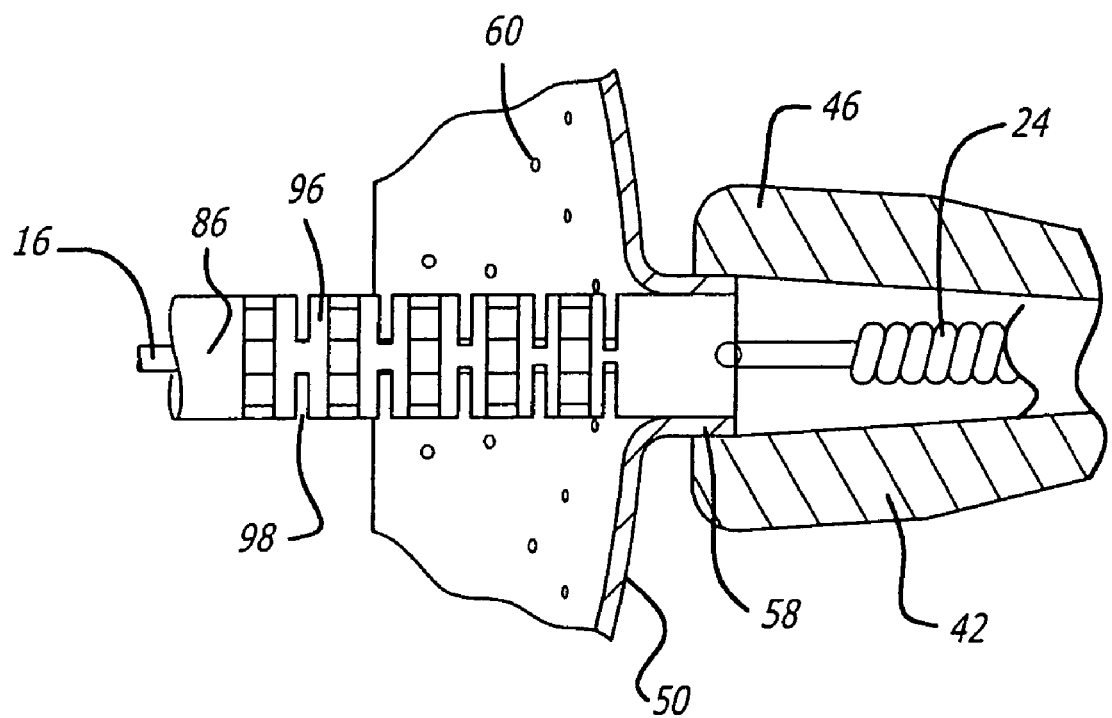
FIG. 14 is a partly cross-sectional view taken along the lines 14—14 in FIG. 13.

In a fourth version of the first embodiment of the invention, as illustrated in FIGS. 15–18, the cage 48 is foreshortened, and comprises the proximal portion 52 thereof, which does not include a distal portion 54 thereof. In the form of FIGS. 15–16, the distal end 58 of the filter material 50 is folded over prior to deployment, and expands upon deployment, and the distal portion 96 of the hypotube 92 extends beyond the distal end 58 of the cage 48. In the form shown in FIGS. 17–18, the proximal portion 94 of the hypotube 92 is spaced from the proximal end 56 of the cage 48 before deployment thereof, and abuts the proximal end 56 of the cage 48 upon deployment thereof. Also, the distal portion 96 of the hypotube 92 is variably flexible, as seen in FIG. 14.

Figure 21:
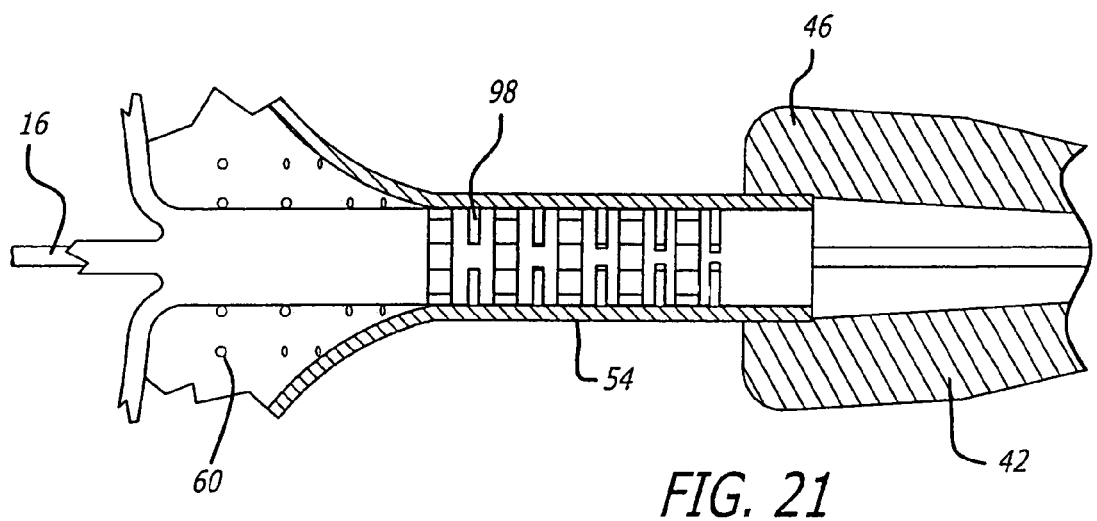
FIG. 21 is a partly cross-sectional view taken along the line 21—21 in FIG. 20.
Figure 22:
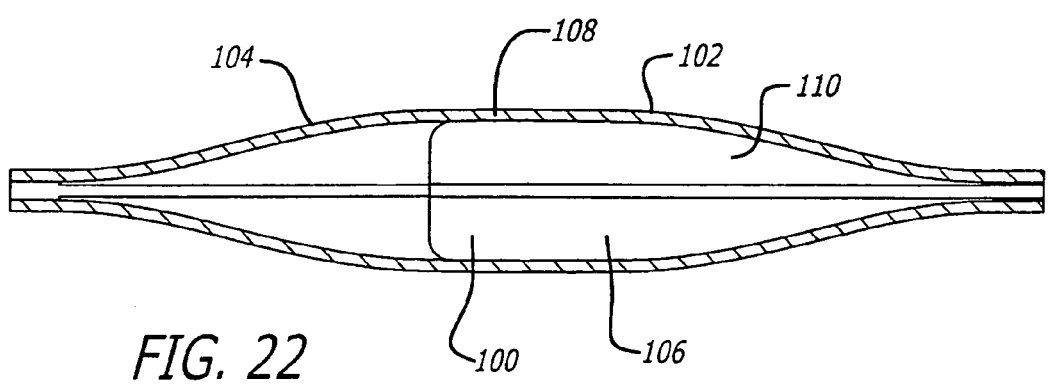
FIG. 22 is an elevational partly-sectional view of a system in a second embodiment of the present invention, including a male mandrel element, and expandable material extending thereover.
Figure 23:
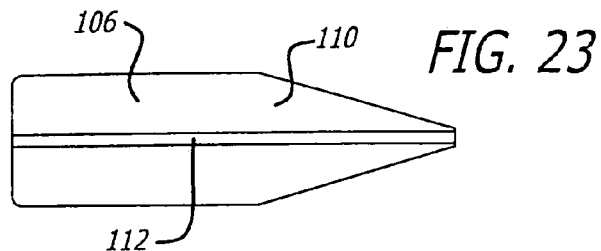
FIG. 23 is an elevational cross-sectional view of a male mandrel element, in the second embodiment of the invention.
Figure 24:
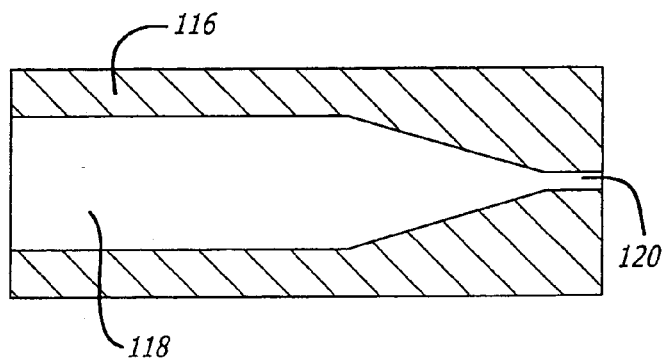
FIG. 24 is an elevational cross-sectional view of a female die element in the second embodiment.
Figure 25:
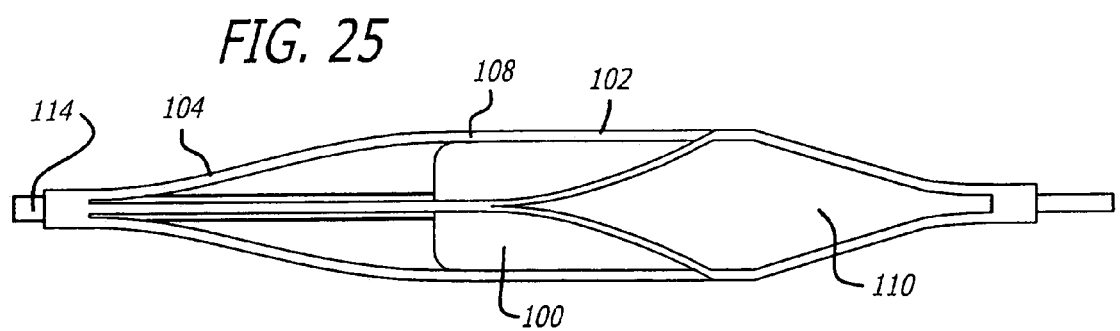
FIG. 25 is an elevational view of a male mandrel element, an alignment pin, and a cage in the second embodiment of the invention.
Figure 26:
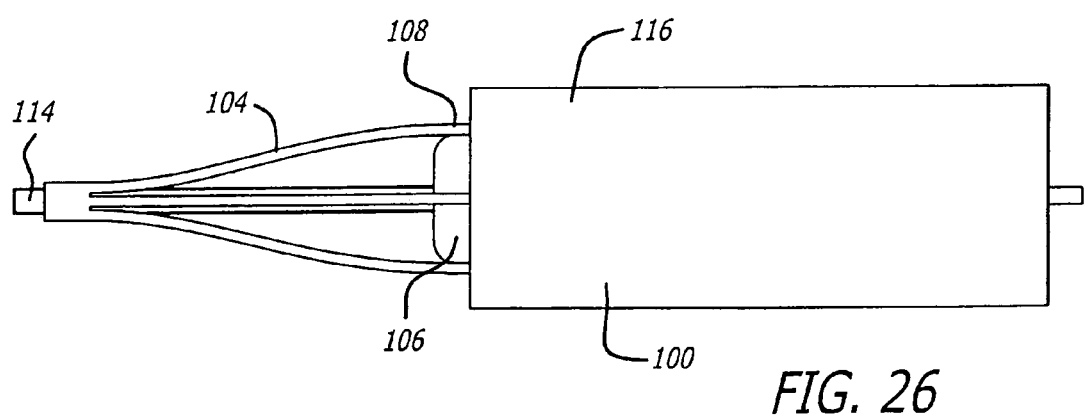
FIG. 26 is a similar view of the second embodiment of the present invention as in FIG. 25, with a female die element extending about the cage and the male mandrel element.

The cage 48 is narrowed towards the distal portion 54 thereof, so as to function as a foreshortened cage, in a fifth version of the first embodiment of the system 10, as shown in FIGS. 19–21. The narrowed distal portion 54 of the cage 48 is variably flexible, as seen in an enlarged view in FIG. 21, to provide a substantially uniformly increasing flexibility profile towards the distal portion 54. The filter material 50 is secured at the proximal end 52 and distal end 58 thereof to the cage 48, so as to enable expansion thereof, as depicted in FIG. 20.

Referring to FIGS. 22–29, in a second embodiment in accordance with the invention, for example, a system 100 is provided for enabling expandable material 102 to be formed into an expanded configuration of a cage 104, which is a version of the cage 48. The system 100 enables forming a cage 104 for a filter device to be formed thereby, for capturing embolic material which may be released into a blood vessel during a therapeutic interventional procedure. The system 100 enables the expanded configuration of the cage 104 to provide a substantially uniform pre-formed maximum outer diameter thereof, for maintaining vessel wall opposition in a patient's vasculature upon deployment of the cage 104 at a location distal to an interventional procedure site. The expandable material 102 for forming the expanded configuration of the cage 104 is in the form of a hypotube.

In the second embodiment pursuant to the present invention, as seen in particular in FIGS. 22–26, the system 100 includes a male mandrel element 106 which enables the expandable material 102 to be extended thereover. The male mandrel element 106 includes a maximum outer diameter portion 108 extending along the length thereof, which is substantially uniform and is substantially equal to the maximum inner diameter of the expanded configuration of the cage 104 to be formed thereby. The hypotube form of the expandable material 102 is extendable over the male mandrel element 106. The male mandrel element 106 further includes a tapered section 110, for enabling the expandable material 102 for forming the expanded configuration of the cage 94 to be extended thereover with a gradual transition thereof, so as to minimize failure of the material resulting from fatigue or damage during expansion thereof. The male mandrel element 106 further includes a generally pin-shaped channel 112 therein, to receive a pin 114 for enabling alignment of the other end of the expanded configuration of the cage 104 to be formed thereby.

The system 100 also includes a female die element 116, which enables the expandable material 102 to be formed therein. The female die element 116 is extendable over the male mandrel element 106 and the expandable material 102 to be formed thereby, so as to lock the male mandrel element 106 and the expandable material 102 therein. The female die element 116 has a cavity 118 therein, which is generally Complementary to the male mandrel element 106, and which includes a generally pin-shaped channel 120 therein. The maximum inner diameter of the cavity 118 of the female die element 116 is substantially uniform, and is substantially equal to the maximum outer diameter 84 of the expanded configuration of the cage 104 to be formed thereby.

Figure 27:
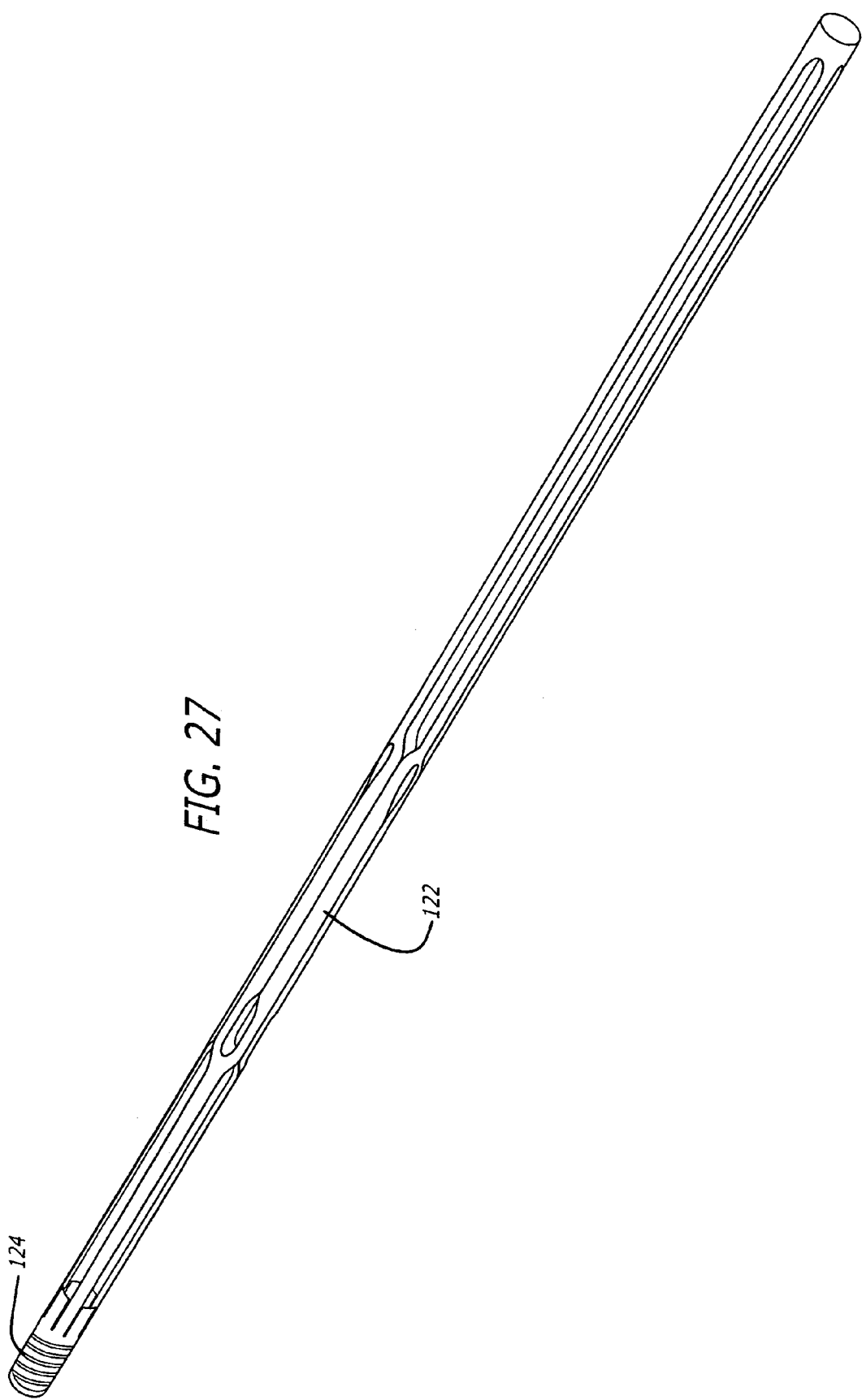
FIG. 27 is an elevational view of a tube of material for forming the struts of a cage, and a spring at one end thereof, in the second embodiment.

As depicted in FIGS. 27–29, a plurality of struts 122 for a cage 104 may be formed from a tube of material, including a spring 124 at an end thereof, to enable one end of the cage 104 to be in tension, and the other end to be in compression, so as to aid in the bending of the system 100, and the tracking and deploying thereof, in the tortuous vasculature 12. Alternatively, a pair of springs, as 124, may be positioned at each end of the tube of strut-forming material. The thin compressed wrapped form of the struts 122 for supporting the expandable material 102 in the cage 104, as they are formed by a laser, is shown in FIG. 27, with the flattened rolled out form thereof seen in FIG. 28, and the expanded form thereof in a cage 104 illustrated in FIG. 29.

Referring to FIGS. 1–21, in a method for the use of the first embodiment of a system in accordance with the present invention, for example, the system 10 enables movement thereof through the patient's blood vessel 12 to the location distal to the area of treatment 14 for deployment of the filter device 30, and seals off the inside wall 28 of the blood vessel 12 to enable the capture of embolic material 32. The filter device 30 and the obturator 42 are assembled, and the proximal stop 76 and the distal stop 78 are mounted on the guide wire with the space 80 therebetween. The inner diameter of the filter device 30, for example, is at least slightly larger than the outer diameter of the tip coil 20, and the at least one tab 82 is pivotable, so as to enable the filter device 30 to be inserted over the tip coil 20. The assembly of the filter device 30 and the obturator 42, for example, is inserted over the tip coil 20 to the position where the tabs 82 snap-fit into the space 80 between the proximal stop 76 and the distal stop 78 mounted on the guide wire 16, so as to snap-fit the filter device 30 to the distal end 22 of the guide wire 16, for efficient engagement therewith. The delivery sheath is extended over the guide wire 16 so as to enclose the filter device 30 therein, and such that the distal portion 40 of the delivery sheath 38 substantially abuts the proximal end 44 of the obturator 42.

The system 10 is positioned in the patient's vasculature 12 utilizing any one of a number of different methods. In one preferred method of positioning the system 10, the delivery sheath 38, with the filter device 30 therein, is inserted into and extended through the patient's vasculature 12, to cross the stenosis in the blood vessel 12, so as to extend to a position distal to the interventional procedure site 14. The guide wire 16 is rotatable during insertion thereof through the patient's vasculature 12, to enable guiding and directing thereof. The snap-fitted filter device 30 is rotatable on the guide wire 16 independent of rotation of the guide wire 16, during insertion of the filter device 30 through the patient's anatomy 12, to inhibit entanglement thereof, while the filter device 30 is also inhibited from translational movement thereof. The foreshortened length of the filter device 30 enables it to be less affected by confined spaces, such as sharp bends and curves, in moving through the patient's anatomy, including tortuous vasculature. The delivery sheath 38 is then withdrawn, enabling the filter device 30 to deploy so as to capture embolic material 32 which may be released in the blood vessel 12 during the interventional procedure.

After the delivery sheath 38 is withdrawn, the filter device 30, snap fitted to the guide wire 16 at the proximal portion 52 of the cage 48 such that the tabs 82 extend between the proximal stop 76 and the distal stop 78, is released from being enclosed in the delivery sheath 38. The filter device 30 then expands into its pre-formed heat-treated shape, with the maximum outer diameter portion 84 thereof bearing against the inside wall 28 of the blood vessel 12. The expansion of the filter device 30 into its pre-formed heat-treated shape, with the maximum outer diameter portion 84 pressing against the inside wall 28 of the blood vessel 12, seals off the inside wall 28 of the blood vessel 12, and inhibits the formation of a gap between the filter device 30 and the blood vessel wall 28, through which embolic material 32 may otherwise flow. The filter material 50 expands with the flow of blood in the blood vessel 12 therethrough, to capture embolic material 32 which may be released during the interventional procedure.

Figure 4:
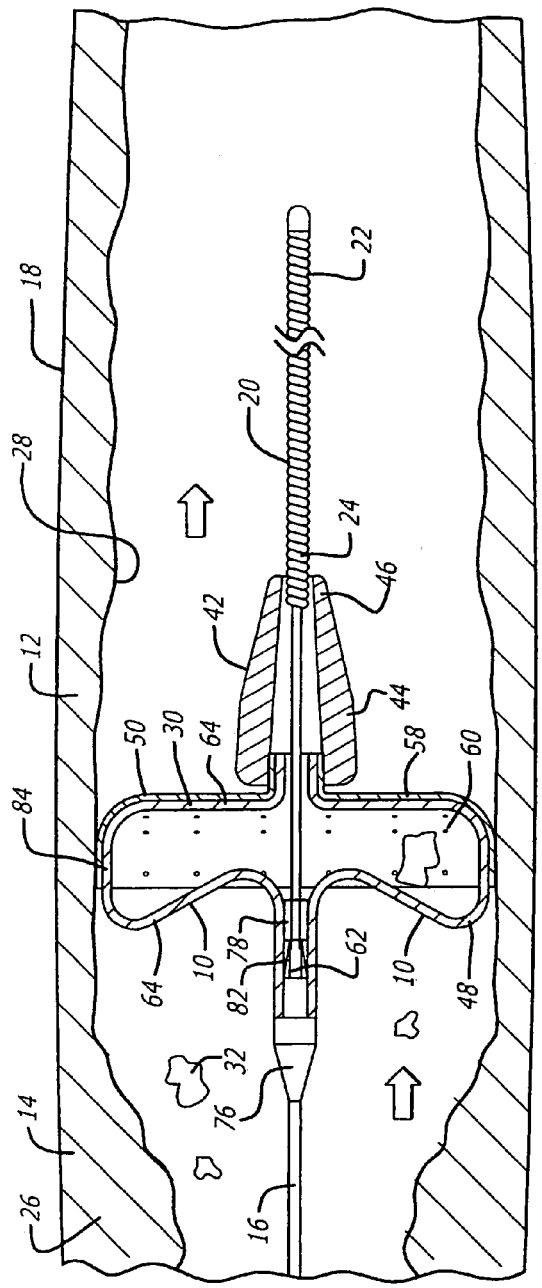
FIG. 4 is a similar view as in FIG. 2, depicting another form of a basket in the first version of the first embodiment of the invention, in expanded condition.

In the first version of the first embodiment of the present invention, as seen in FIGS. 1–3, the cage 48 expands into a pre-formed heat treated generally-rectangular shape, or a generally-cylindrical shape, in the form in FIGS. 1–3, and into a generally s-shape for the proximal portion 52 of the cage 48 in FIGS. 4–5. The generally s-shaped proximal portion 52 of the cage 48 absorbs pulsations in the patient's blood vessel 12. The filter material 50 expands between the maximum outer diameter portion 84 and the distal portion 54 of the cage 48 to which it is secured. It further expands in accordance with the contours of the ring 70 and the distal ribs 68 about which it extends, as seen in FIG. 5. The filter material 50, in the second version of the first embodiment of the invention, as illustrated in FIGS. 6–9, expands between the cage maximum outer diameter portion 84 and the distal portion 96 of the hypotube 92 to which it is secured.

As shown in FIGS. 10–14, in the third version of the first embodiment thereof, the filter material 50 expands from the folded over condition thereof to extend between the maximum outer diameter portion 84 of the cage 48, and the obturator 42 and the variably flexible distal portion 96 of the hypotube 92 between which it is secured, in the form in FIGS. 10–11 and 14. In the form in FIGS. 12–14, the filter material 50 expands so as to extend between the maximum outer diameter portion 84 of the cage 48 and the variably flexible distal portion 96 of the hypotube 92 to which it is secured. The filter material 50, in the fourth version of the first embodiment of the invention as depicted in FIGS. 15–18, expands, in the form shown in FIGS. 15–16, from the folded over condition thereof to extend between the maximum outer diameter portion 84 of the cage 48 and the extended distal portion 96 of the hypotube 92 to which it is secured. In the form in FIGS. 17–18, the filter material 50 expands from the cage maximum outer diameter portion 84 to the hypotube extended distal portion 96 and about the tip coil proximal end 24. As illustrated in FIGS. 19–21, in the fifth version of the first embodiment thereof, the filter material 50 expands in the distal direction from the maximum outer diameter portion 84 of the cage 48 to the variably flexible extended distal portion 54 of the cage 48 to which it is secured.

Referring to FIGS. 22–29, in a method for the use of the second embodiment of a system in accordance with the present invention, for example, the system 100 enables the formation of expandable material 102 into an expanded configuration of a cage 104 for capturing embolic material 32. In particular as seen in FIGS. 22–26, a pin 114 is inserted into the generally pin-shaped channel 112 in the male mandrel element 106 for alignment thereof. The expandable material 102 is extended over the maximum outer diameter portion 108 of the male mandrel element 106, so as to form the maximum inner diameter of the expanded configuration of the cage 104 to be formed thereby. The cavity 118 of the female die element 116 is extended over the male mandrel element 106 and the expandable material 102, to form the maximum outer diameter portion 108 of the cage 104 to be formed thereby. As depicted in FIGS. 27–29, the struts 122 for supporting the expandable material 102 in the cage 104 are formed as a thin compressed wrapped tube by a laser, and the spring 124 is wrapped about an end thereof. Ball bearings are placed between the generally v-shaped portions of the tube, and are heated to expand outwardly, to form the heat-treated shape of the cage 104.

In accordance with the present invention, the particular embodiments set forth above of the system 10 for filtering embolic material are capable of being positioned in a blood vessel, and of the system 90 are capable of forming an expanded configuration of a device for filtering embolic material. However, other forms of the system 10 and the system 90 may be utilized with the present invention without departing from the spirit and scope of the invention. For example, the system 10 and the system 90 may be comprised of other forms of material. Additionally, while the system 10 and the system 90 are shown as in various shapes in the embodiments herein, they can be formed in any one of a number of different shapes depending upon the construction desired.

Further, the various components may be joined by suitable adhesives such as acrylonitrile based adhesives or cyanoacrylate based adhesives. Heat shrinking or heat bonding may also be employed where appropriate. Plastic-to-plastic or plastic-to-metal joints can be effected by a suitable acrylonitrile or cyanoacrylate adhesive. Variations can be made in the composition of the materials to vary properties as needed. Based on the present disclosure, other adhesives and applications are known to one skilled in the art.

In view of the above, it is apparent that the system and method of the first embodiment of the present invention enhances substantially the effectiveness of performing interventional procedures by providing a filter device for filtering embolic material, to be snap-fitted for engagement with a guide wire, and independently rotatable relative to the guide wire, for efficient assembly, insertion and removal thereof. The system and method further enable the filter device to expand against the inner wall of a blood vessel so as to seal off the inner surface thereof, to inhibit gap formation and the passing of embolic material therethrough. The system and method also include a foreshortened cage, which is shortened to enable effective insertion thereof through tortuous anatomy. The system and method of the second embodiment of the present invention substantially enhance the effectiveness of performing interventional procedures, by enabling expandable material to be efficiently formed into an expanded configuration of the cage for the filter device, so as to provide a substantially uniform maximum outer diameter thereof for maintaining vessel wall opposition to the patient's vasculature, to inhibit embolic material from passing therethrough.

While the present invention has been described in connection with the specific embodiments identified herein, it will be apparent to those skilled in the art that many alternatives, modifications and variations are possible in light of the above description. Accordingly, the invention is intended to embrace all such alternatives, modifications and variations as may fall within the spirit and scope of the invention disclosed herein.

What is claimed is:

1. A system for pre-forming an expandable material into an expandable cage for a filter device, comprising:
    a male mandrel element having a particular shape which forms the shape of the inner surface of the expandable cage, the male mandrel element allowing the expandable material to be deformed, bent or heat set to retain the particular shape of the male mandrel element, the male mandrel element having a channel formed therein;
    a female die element having a cavity formed therein of a particular shape which forms the outer surface of the expandable cage, the female die element having a length which extends for at least a portion of the length of the male mandrel member, the particular shape of the cavity of the female die element allowing the expandable material to be deformed, bent or heat set to retain the particular shape of the cavity; and
    a pin receivable within the channel formed in the male mandrel element for maintaining the expandable material aligned relative to the male mandrel element.

2. The system of claim 1, further including a heat source for heat setting at least a portion of the expandable material to the particular configuration created by the male mandrel element and the female die element.

3. The system of claim 2, wherein the male mandrel element includes a main section, a distal end and a tapered section which extends from the distal end of the main section.

4. The system of claim 1, wherein the channel formed in the male mandrel element extends through the male mandrel element and the pin is sufficiently long to be received in the channel while allowing the ends of the pin to extending outside of the channel.

5. The system of claim 4, wherein the female die element has a channel formed therein for receiving the pin to maintain the expandable material aligned relative to the female die element.

6. The system of claim 1, wherein the expandable material is cold worked into the particular shape of the male mandrel element and the female die element.

7. A system for forming the expanded configuration of an expandable cage for a filter device from a length of tubing, the system comprising:
- a male mandrel element having a particular shape which forms the shape of the inner surface of the expandable cage, the male mandrel element allowing the length of tubing to be deformed or bent to retain the particular shape of the male mandrel element, the male mandrel element having a channel formed therein;
- a female die element having a cavity formed therein of a particular shape which forms the outer surface of the expandable cage, the female die element having a length which extends for at least a portion of the length of the male mandrel member, the particular shape of the cavity of the female die element allowing the length of tubing to be deformed or bent to retain the particular shape of the cavity; and
- a pin receivable within the channel formed in the male mandrel element for maintaining the expandable material aligned relative to the male mandrel element.

8. The system of claim 7, further including a heat source for heat setting at least a portion of the length of tubing to the particular configuration created by the male mandrel element and the female die element.

9. The system of claim 7, wherein the male mandrel element includes a main section, a distal end and a tapered section which extends from the distal end of the main section.

10. The system of claim 7, wherein the channel formed in the male mandrel element extends through the male mandrel element and the pin is sufficiently long to be received in the channel while allowing the ends of the pin to extending outside of the channel.

11. The system of claim 10, wherein the female die element has a channel has a channel formed therein for receiving the pin to maintain the length of tubing material aligned relative to the female die element.

12. The system of claim 7, wherein the length of tubing is cold worked into the particular shape of the male mandrel element and the female die element.

* * * * *

UNITED STATES PATENT AND TRADEMARK OFFICE
CERTIFICATE OF CORRECTION

PATENT NO. : 7,097,440 B2
APPLICATION NO. : 10/676181
DATED : August 29, 2006
INVENTOR(S) : John E. Papp et al.

It is certified that error appears in the above-identified patent and that said Letters Patent is hereby corrected as shown below:

Column 2,
Line 24, delete "titanum" and insert --titanium--.

Column 11,
Line 44, delete "Complementary" and insert --complementary--.

Column 15,
Line 8, delete "extending" and insert --extend--.

Column 16,
Line 19, delete "extending" and insert --extend--.
Line 22, delete the second occurrence of "has a channel".

Signed and Sealed this

Thirteenth Day of March, 2007

JON W. DUDAS
*Director of the United States Patent and Trademark Office*